United States Patent
Slaton

(10) Patent No.: US 10,507,073 B2
(45) Date of Patent: Dec. 17, 2019

(54) PACKAGE ASSEMBLY FOR STERILE AND CONVENIENT INSERTION OF DILATOR INTO SHEATH

(71) Applicant: TERUMO MEDICAL CORPORATION, Somerset, NJ (US)

(72) Inventor: Peter Slaton, Newark, DE (US)

(73) Assignee: TERUMO MEDICAL CORPORATION, Somerset, NJ (US)

( * ) Notice: Subject to any disclaimer, the term of this patent is extended or adjusted under 35 U.S.C. 154(b) by 589 days.

(21) Appl. No.: 15/266,913

(22) Filed: Sep. 15, 2016

(65) Prior Publication Data
US 2018/0071044 A1    Mar. 15, 2018

(51) Int. Cl.
*A61B 50/30*    (2016.01)
(52) U.S. Cl.
CPC .................................... *A61B 50/30* (2016.02)
(58) Field of Classification Search
CPC ......... A61B 50/30; A61B 50/00; A61B 50/31; A61F 2/0095
USPC ........................................................ 206/438
See application file for complete search history.

(56) References Cited

U.S. PATENT DOCUMENTS

| | | | | |
|---|---|---|---|---|
| 4,262,800 A * | 4/1981 | Nethercutt | .......... | A61B 1/00144 206/364 |
| 7,285,253 B2 * | 10/2007 | Moriyama | ............. | A61B 1/121 134/170 |
| 2006/0011501 A1 * | 1/2006 | Itou | ..................... | A61M 25/002 206/370 |
| 2015/0068941 A1 * | 3/2015 | Caron | ................. | A61M 25/002 206/364 |

* cited by examiner

*Primary Examiner* — King M Chu

(57) ABSTRACT

A package assembly for an elongate surgical device in which two or more elongate surgical devices are secured and oriented in a coiled configuration so that a distal end of a first elongate surgical device may be inserted into a proximal end of a second elongate surgical device. In this assembly, the elongate surgical devices remain in a protected coiled state in the package while in the sterile field and so that a medical professional may prep the elongate surgical devices without removing from the package prior to use. In this package assembly, the elongate surgical devices reduce space required and eliminate the risk of damage to the devices and/or the chance of the elongate surgical devices become unsterile prior to use.

6 Claims, 3 Drawing Sheets

PACKAGE ASSEMBLY FOR STERILE AND CONVENIENT INSERTION OF DILATOR INTO SHEATH

TECHNICAL FIELD

The present technology relates generally to packaging for surgical devices. More specifically, this disclosure relates to packaging for use with surgical devices, particularly catheters, guidewires, sheaths and dilators, such that when the packaging incorporates a sheath and dilator, for example, the dilator may be inserted into the sheath in a sterile manner and without removing the sheath from the packaging, thus reducing the possibility of the dilator and sheath becoming non-sterile.

BACKGROUND

A surgical operation or procedure such as a diagnosis or a medical treatment in which a catheter is used has been popularized because it imposes a comparatively low burden on a patient. Such a surgical operation as just mentioned is performed by introducing various instruments beginning with a catheter into a puncture hole or the like formed in an arm, a leg or another site of the patient and extending to an artery.

In a surgical procedure such as that described above, a wide variety of medical devices and drugs are used, perhaps involving up to several tens of medical devices and drugs, including throwaway unwoven fabrics (drapes) adapted to be spread on an imaging intensifier, devices and drugs such as an antiseptic used at a preparation stage prior to a surgical procedure (such as a set for drip fusion including a needle and a tube for dripping the heparin of an antithrombotic drug to a patient), surgical gowns for doctors, absorbent cottons, tweezers, forceps and scissors for applying antiseptic, skin cutting surgical knives used after a surgical operation is started, indwelling needles, introducer sheaths and dilators, guide wires for the introducer, syringes, angiographic catheters, guide wires for the angiographic catheter, angiographic agent, microcatheters and so forth which are used for a diagnosis or a medical treatment, PTCA (Percutaneous Transluminal Coronary Angioplasty) guiding catheters (shape for the right side of the heart, shape for the left side and so forth), PTCA guide wires, PTCA balloon catheters, balloon dilating devices (indeflators), stent delivery catheters, hemostatic devices used after an operation or procedure, and beakers, cups and so forth for temporarily keeping various drugs and agents. To help prevent infection, most of these medical devices, drugs and the like are of the throwaway type.

Sheath and dilator systems are typically packaged in the same package but separate from each other. The reason for this is that there is a risk of deformation or damage to the valve which limits blood loss during endovascular procedures.

For longer devices this can cause an issue because the package sizes become very long and hard to handle. Additionally, combining the dilator into the sheath can be cumbersome and risk contamination.

For example, during a surgical procedure, long dilators and their corresponding sheaths are removed from sterile packaging by a medical practitioner and are often laid upon the body of the patient as part of preparation for inserting the dilator within the sheath, prior to using them to gain vascular access.

However, due to their length there is risk for the long dilator and the long sheath to come in contact with the floor, or some other non-sterile surface, or become damaged while prepping the dilator, or when combining/inserting the dilator into the sheath. Contact with the operating room floor, or other non-sterile surface, renders both the dilator and the sheath non-sterile and typically requires a replacement device to be used. Prepping another device is both time consuming and costly.

U.S. Pat. No. 7,234,597 teaches a package for an elongate surgical device, such as a catheter, includes an elongate tube formed into a coil configuration with a first coil portion disposed adjacent to a second coil portion. In this package, a thermal weld bonds the coil portions in a fixed relationship and with a strength sufficient to prevent peeling the first coil portion from the second coil portion. The surgical device can then be loaded into the tube, pouched and sterilized for distribution.

Existing devices typically provide for separate sterile packaging for long dilators and long sheaths. However existing devices do not permit sterile insertion of the dilator within the sheath while in shared packaging and do not reduce the possibility of either the dilator or sheath becoming non-sterile by allowing the devices to be combined while still in the package.

In view of the foregoing, there continues to be a need for an elongated surgical device packaging in which elongated surgical devices such as a sheath and dilator, may be packaged separately but secured and oriented in such a coiled configuration that facilitates inserting the dilator into the sheath without removing the sheath from its coil.

SUMMARY

In certain embodiments, the present technology is directed to a coiled package design that enables the user to insert a dilator into sheath without removing the dilator from the package before inserting the sheath. This allows long products to stay in a protected coiled state while in the sterile field, which reduces space required and the risk of damage to or dropping of the product In accordance with one embodiment, the design of the package would be a coiled sheath and dilator that allows the user to prepare and hydrate the dilator and sheath without removing them from their holders, as well as combine them in a coiled state.

In an aspect of an embodiment, the dilator and sheath will be packaged separately but will be secured and oriented in such a way that facilitates inserting the dilator into the sheath without removing the sheath from its coil.

The packaging of the instant disclosure seals the long dilator and long sheath in one sterile package. In the package according to the instant disclosure, the sheath is contained in a spiral tube in the sterile package shared with the dilator.

In another aspect, the dilator may optionally be contained within a spiral tube.

The orientation of the dilator with respect to the sheath in the instant disclosure, while both are within the sterile packaging, is such that the dilator can be fed into the sheath without removing the sheath from the protective tubing.

In the instant disclosure, both the dilator and the sheath may remain coiled in their packaging until vascular access is required during the surgical procedure.

Additionally, the coiled nature of the design of the invention saves space and time by permitting sterile insertion of the dilator within the sheath and also reduces the possibility of either the dilator or sheath becoming non-sterile.

DETAILED DESCRIPTION

An embodiment of the present disclosure will be described below with reference to the drawings. The dimensional ratio of the drawings is exaggerated for convenience of description and is different from the actual ratio in some cases.

Figure 1:
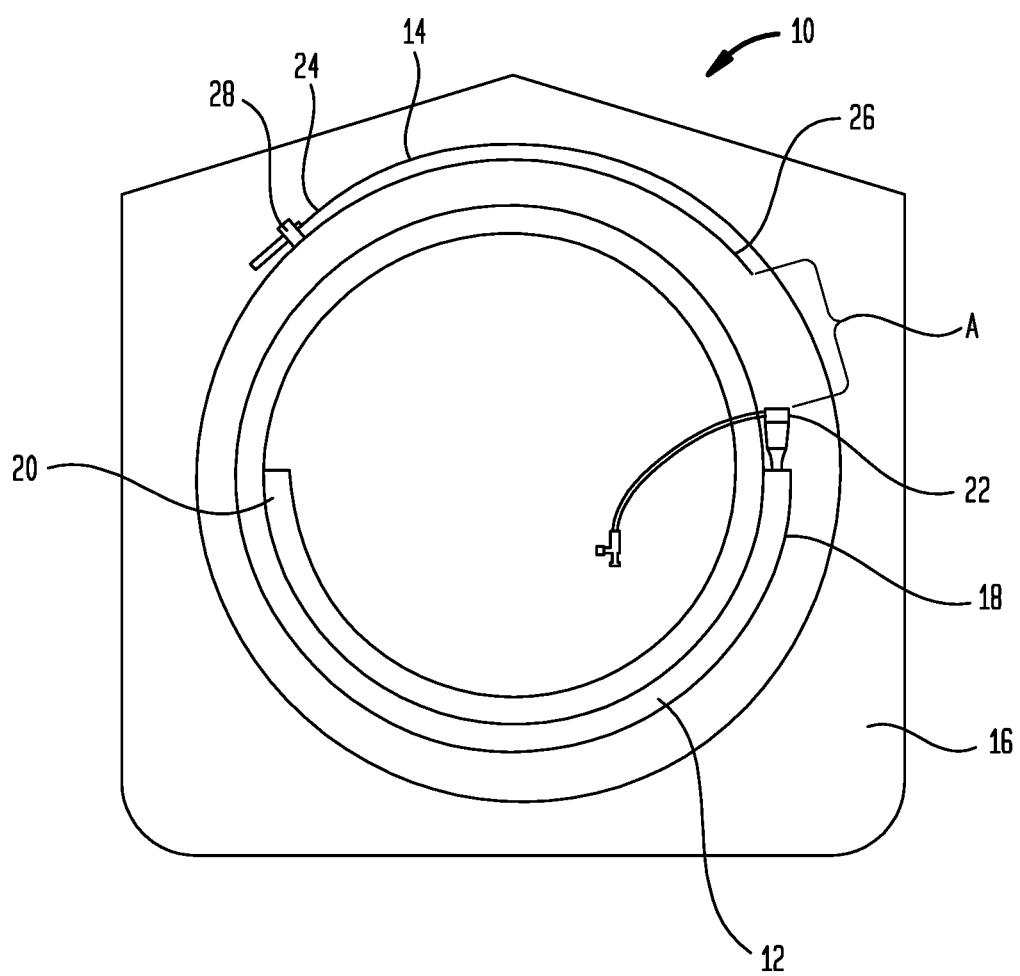
FIG. 1 illustrates a sheath and dilator according to one aspect in which the sheath and dilator are secured to a backing card.

In an embodiment of the instant disclosure, a surgical dilator and sheath are sealed within one sterile package. FIG. 1 illustrates a packaging assembly 10 wherein a sheath 12 and a dilator 14 are secured on a backing card 16, which may be a die-cut card.

Sheath 12 includes a proximal end 18 and a distal end 20. Proximal end 18 will typically include a hub 22 that allows manipulation of the sheath by a medical professional. An internal passageway or lumen extends between proximal end 18 and distal end 20 of sheath 12. Dilator 14 includes a proximal end 24 and a distal end 26. Dilator 14 will typically include a hub 28 on the proximal end 24. An internal passageway or lumen extends between proximal end 24 and distal end 26 of dilator. Sheath hub 22 and dilator hub 28 may include one or more ports and/or arms attachment of additional devices and/or for communication with the inside passageway or lumen of the sheath and dilator respectively. Dilator 14 advantageously includes a dilation member (not shown). The dilation member may be a balloon, although the disclosure is not limited to just a balloon. The balloon is typically made of any flexible material, so that it expands upon injection of a fluid (liquid or gas such as air). Those of ordinary skill in the art will understand that other types of dilation members may be utilized and are contemplated by the instant disclosure.

In the embodiment illustrated in FIG. 1, sheath 12 and dilator 14 are oriented in coiled configuration such that dilator 14 is coiled around the sheath 12 and such that the distal end 26 of dilator 14 is positioned opposite proximal end 18 of sheath 12. Typically a gap (indicated by "A") is provided between distal end 26 of dilator 14 and proximal end 18 of sheath 12. In this configuration, distal end 26 of dilator 14 may be caused to enter proximal end 18 of sheath 12, typically through hub 22 and to pass through the internal passageway or lumen of sheath 12.

The backing card 16 as shown in FIG. 1 may be cardboard, corrugated paperboard, heavy plastic or any surface upon which sheath 12 and dilator 14 may be secured. In an embodiment of the instant disclosure, tabs may be formed in the backing card 16 to define die cuts which secure sheath 12 and dilator 14 thereto. The present disclosure is not limited in the securing mechanism used and securing mechanisms to known to those having ordinary skill in the art, such as for example but not limited to, thermal plastic sealing and ultrasonic sealing, are contemplated.

With reference to the embodiment illustrated in FIG. 1, during a surgical procedure, the package assembly 10 is opened, dilator 14 is prepped and/or hydrated by the medical professional, removed from the backing card 16 and easily inserted into coiled sheath 12. The combined dilator/sheath assembly is then removed completely from the backing card 16 for use in the surgical procedure.

In an alternative embodiment, sheath 12 secured to backing card 16 may further include a sheath tube coiled and secured to the die-cut card 16 and within which sheath 12 is positioned. Obviously, the sheath tube will have an inner diameter that is larger than the outer diameter of sheath 12 so that sheath 12 can be inserted into and contained within the sheath tube.

In an alternative embodiment, dilator 14 may also be contained within a tube in a coiled configuration that is secured to backing card 16. In this manner, both the dilator and sheath may be positioned within tubing that is double coiled and secured upon the backing card 16. In this embodiment, when the package is opened, dilator 14 is removed from its coiled tube and then prepped/hydrated and inserted into sheath 12, which is then removed from its own coiled tube. The dilator and sheath are thus removed from the backing card 16 and are fully sterile.

Figure 2:
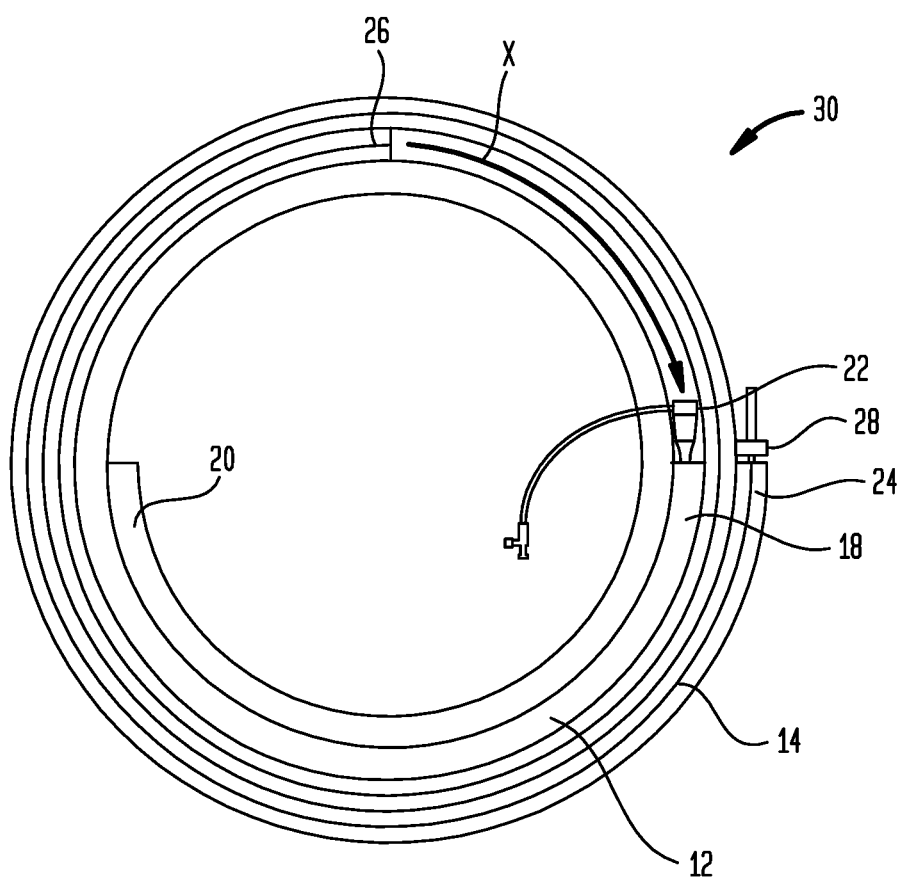
FIG. 2 illustrates a sheath and dilator according to one aspect in which the sheath and dilator are double coiled within a packaging assembly
Figure 3A:
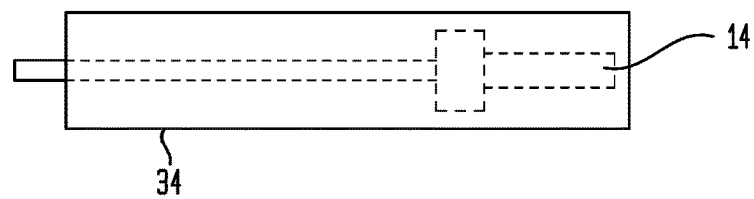
FIG. 3A illustrates a side view of a large internal diameter tubing having a dilator positioned within the tubing.
Figure 3B:
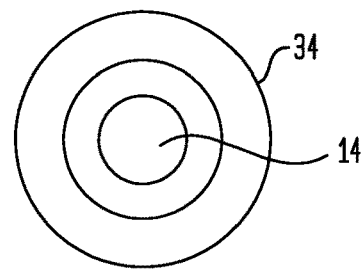
FIG. 3B is a cross-section view of a large internal diameter tubing having a dilator positioned within the tubing.

FIG. 2 illustrates a double coil tubing package assembly 30 in which sheath 12 and dilator 14 are positioned within protective tubing. In FIG. 3, sheath 12 is positioned within sheath protective tubing 32 and dilator 14 is positioned within dilator protective tubing 34. As with the embodiment shown in FIG. 1, the sheath 12 and dilator 14 are coiled in an orientation such that the distal end 26 of dilator 14 is spaced from proximal end 18 of sheath 12 to define a gap so that the distal end 26 of the dilator 14 can be pushed or pulled through the gap space (indicated by "X") to enter sheath 12 via sheath hub 22. The space defined between the distal end 26 of dilator 14 and proximal end 18 of sheath 12 is advantageously in the range from about 2 in. to about 4 in. In this embodiment, dilator protective tubing 34 has an internal diameter large enough so that dilator hub 28 may be positioned within the dilator protective tubing 34 as shown in FIG. 3A. FIG. 3B illustrates a cross section view of the dilator protective tubing 34 within which dilator 14 and dilator hub 28 are positioned. It is also contemplated that the double coil tubing package of FIG. 2 may include the sheath 12 within sheath protective tubing 32 but the dilator 14 is coiled about the sheath 12 in protective tubing 32 without dilator protective tubing 34.

Figure 4A:
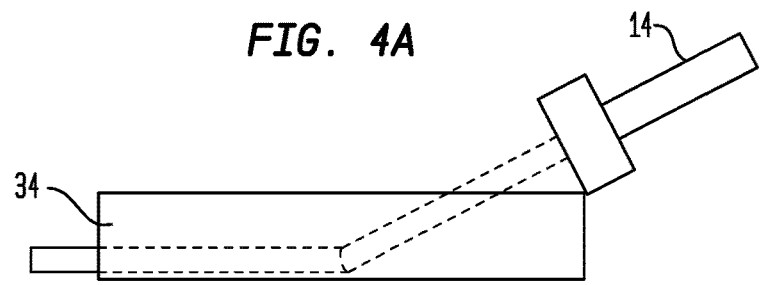
FIG. 4A illustrates a side view of a split tubing for receiving a dilator through a gap formed by the split in the tubing.
Figure 4B:
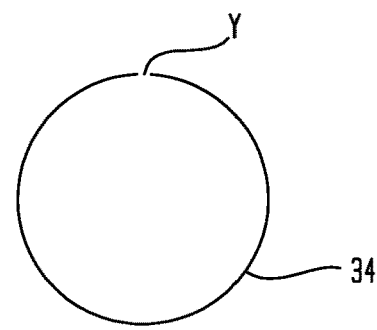
FIG. 4B is a cross-section view of a split tubing for receiving a dilator through a gap formed by the split in the tubing.

In another embodiment, dilator protective tubing 34 may include a split or slit along the entirety of its length longitudinally. The split in the dilator protective tubing 34 defines a cap between the opposing sides of the dilator protective tubing 34 such that the dilator 14 can be inserted or pushed through the gap so it can be positioned within the interior of the dilator protective tubing. FIG. 4A provides a side view of the split tubing as herein described. FIG. 4B illustrates a cross section the split tubing, such as the dilator protective tubing 34 and showing the gap in the tubing (indicated by "Y") to allow the dilator to be pushed through into the interior of the tubing.

In an embodiment in accordance with the instant disclosure, the orientation of the dilator with respect to the sheath is such that the dilator can be fed into the sheath without removing the sheath from the protective tube, while both are within the sterile packaging.

In one embodiment, both the dilator and the sheath may remain coiled in their packaging until vascular access is required during the surgical procedure.

It is the coiled nature of the packaging that saves space and time by permitting the sterile insertion of the dilator within the sheath, and also reduces the possibility of either the dilator of sheath from becoming non-sterile.

Sheath as used herein will be well known to those having ordinary skill in the art and may include for example, but not limited to, PINNACLE® TIF TIP™ Introducer Sheaths, GLIDESHEATH™ Introducer Sheaths and PINNACLE® DESTINATION® Guiding Sheaths, all from Terumo Medical Corporation, Somerset, N.J.

Dilator as used herein will be well known to those having ordinary skill in the art and may include for example, but not limited to, Terumo PINNACLE® DESTINATION® and Terumo PINNACLE® PRECISION® dilators.

In an alternative embodiment, a guidewire may also be used along with the dilator and sheath. Guidewire as used herein will be well known to those having ordinary skill in the art and may include for example, but not limited to, Terumo GLIDEWIRE® and RUNTHROUGH® guidewire products.

The die-cut card 16 as disclosed herein may comprise, but are not limited to, cardboard, corrugated paper, heavy-duty plastic, and the like.

Protective tubing as disclosed herein may comprise tubing made from for example but not limited to nylon, polyethylene, polyvinyl chloride (PVC) and the like.

The methodology to produce the double coil packaging assembly uses existing manufacturing methods to secure the sheath and dilator tubing to the card. Special processing would, however, be required to prepare the split tubing as illustrated in FIG. 4B. In one aspect, the tubing would first have to be split so the cut in the tubing is directing down the middle of the tube along its longitudinal length. Then while securing the split tubing to the card the manufacturer would have to ensure the split in the tubing would be facing up in order to accommodate the dilator within as show in FIG. 4B. In one aspect, this could potentially be done with a mold that has a notch in it to guide the tubing through the mold while keeping the split in the tubing in an upward orientation.

Although the present technology has been described in relation to particular embodiments thereof, these embodiments and examples are merely exemplary and not intended to be limiting. Many other variations and modifications and other uses will become apparent to those skilled in the art. The present technology should, therefore, not be limited by the specific disclosure herein, and may be embodied in other forms not explicitly described here, without departing from the spirit thereof.

What is claimed is:

1. A package assembly for an elongate surgical device, comprising:
    two or more elongate surgical devices; each of the two or more elongate surgical devices having a proximal end and a distal end;
    the two or more elongated surgical devices oriented in a coiled configuration and secured to a surface, wherein the two or more elongate surgical devices are oriented in a coiled configuration such that the distal end of a first elongate surgical device may be inserted into the proximal end of a second elongate surgical device; and
    a protective tube within which the one or more elongate surgical devices is disposed, wherein the protective tube has a slit that extends along a longitudinal length of the protective tube and within which said one or more elongate surgical devices are disposed.

2. The package assembly of claim 1, wherein the first elongate surgical device is a dilator.

3. The package assembly of claim 1, wherein the second elongate surgical device is a sheath.

4. The package assembly of claim 1, wherein the surface is a backing card.

5. The package assembly of claim 4, wherein the backing card is a die-cut card.

6. The package assembly of claim 1, wherein the proximal end of each the elongate surgical devices includes a hub, the hub further comprising one or more arms or ports.

* * * * *